United States Patent [19]
Karlberg et al.

[11] Patent Number: 5,641,966
[45] Date of Patent: Jun. 24, 1997

[54] PROCESS OF MEASURING CHEMICAL AND PHYSICAL PARAMETERS FOR CHARACTERIZATION AND CLASSIFICATION OF AQUEOUS SUSPENSIONS

[75] Inventors: Bo Karlberg, Sollentuna; Mikael Karlsson, Djursholm, both of Sweden

[73] Assignee: Tecator AB, Hoganas, Sweden

[21] Appl. No.: 578,693

[22] PCT Filed: Jun. 28, 1994

[86] PCT No.: PCT/SE94/00605

§ 371 Date: Dec. 27, 1995

§ 102(e) Date: Dec. 27, 1995

[87] PCT Pub. No.: WO95/01560

PCT Pub. Date: Jan. 12, 1995

[30] Foreign Application Priority Data

Jun. 29, 1993 [SE] Sweden ................... 9302242

[51] Int. Cl.⁶ .................................................. G01J 3/00
[52] U.S. Cl. .......................... 258/373; 250/432 R
[58] Field of Search ..................... 250/373, 432 R, 250/435

[56] References Cited

U.S. PATENT DOCUMENTS

| | | | |
|---|---|---|---|
| 4,247,773 | 1/1981 | Nexo et al. | 250/339 |
| 4,800,279 | 1/1989 | Hieftje et al. | |
| 5,242,602 | 9/1993 | Richardson et al. | 210/745 |
| 5,272,346 | 12/1993 | Kaplan et al. | 250/373 |
| 5,420,432 | 5/1995 | Manook et al. | 250/373 |

FOREIGN PATENT DOCUMENTS

| | | |
|---|---|---|
| 0404562A2 | 12/1990 | European Pat. Off. . |
| 3324606A1 | 1/1985 | Germany . |
| 1565988 | 4/1988 | United Kingdom . |
| WO92/16828 | 10/1992 | WIPO . |

OTHER PUBLICATIONS

Ross et al., "Potentiometric Gas Sensing Electrodes", *Pure and Applied Chemistry*, vol. 36, No. 4, 473–487, (1973). no month.

Thomas et al., "Ultraviolet multiwavelength absorptiometry (UVMA) for the examination of natural waters and wastewaters", *Fresenius J. Anal. Chem.*, vol. 338, 234–237, 1990. no month.

Beemster et al., "On–line and In Situ Detection of Nitrates with Ultraviolet–Visible Absorption Spectrometry (UVAS)", American Water Works Association, Water Quality Technology Conference, Nov. 10–14, 1991.

Chemscan, "UV–6100 Analyzer For On–Line Nitrate Analysis" Biotronics Technologies, Inc., no date.

*Primary Examiner*—David P. Porta
*Assistant Examiner*—David Vernon Bruce
*Attorney, Agent, or Firm*—Scully, Scott, Murphy & Presser

[57] ABSTRACT

The present invention relates to a method of determining physical and/or chemical properties in water samples containing suspended substances and/or particles, the physical and/or chemical properties being singly or jointly determined as amount of nitrate, iron, ammonium, phosphate, total nitrogen or total phosphorous; turbidity, chemical oxygen demand (COD) and/or biological oxygen demand (BOD).

8 Claims, 6 Drawing Sheets

PROCESS OF MEASURING CHEMICAL AND PHYSICAL PARAMETERS FOR CHARACTERIZATION AND CLASSIFICATION OF AQUEOUS SUSPENSIONS

TECHNICAL FIELD

Present invention relates to a method of measuring amounts/ of chemical compounds and quality parameters of chemical and physical character in waste water, process water, sea/lake-water etc. Examples of such quality parameters are amounts of nitrate, ammonium, orthophosphate, total nitrogen, total phosphorus and iron as well as chemical oxygen demand (COD) and turbidity. The present invention, furthermore, relates to a method of classification of aqueous suspensions. Data from known categories and classes of aqueous suspensions are thereby collected and analysed, after which unknown samples through measurements can be assigned to any or some of the known classes. Deviations from known class patterns can also be registered.

PRIOR ART

Certain amount and quality parameters are during purification of for example waste water by routine measured in order to monitor the effect of the various purification steps. A measurement of the amounts of nitrate and ammonium during the nitrification and denitrification steps is of a particularly great interest. Ammonium is during the nitrification step oxidised to nitrate by way of air being pumped through the water whereby air oxygen causes the oxidisation. Nitrate is during the denitrification step transformed into nitrogen in that enzymes from certain bacteria catalyze this transformation reaction. It is thereby required that the bacteria are allowed to work in a carbon high-energy environment, for example in a sludge containing organic carbon or in that such an environment is created by addition of for instance methanol or ethanol.

Off-line and on-line measurements of chemical and physical parameters are usually distinguished. Samples are in off-line measurements collected in receptacles thereto designed, often bottles or tubes. Accurately measured amounts of these collected samples are thereafter manually treated by the analytical chemist, thus taking care of filtering, addition of selective reagents, mixing, heating, transferring of the mixture to a detector cell, calculation of the amount by putting the reading in relation to previously performed calibrations and registration and reporting of the result. Certain parts of this chain of logistics can be subject to automation. In some automatic off-line analysers, the only thing the analyst has to do is to put the samples in a sample-changer, after which certain or all parts of aforementioned work chain are carried out automatically. Characterising for all off-line measurements is, however, that the collecting of samples per se and the transfer of these to an analyser/detector of any kind requires a human achievement. In on-line measurements, however, the method is temporarily or permanently linked to the detector in that a continuous supervision of various processing parameters is obtained. This supervision can be completely automated, i.e. without manual work elements.

Commercially available continuous indicators for nitrate and ammonium are often based on electrochemical measuring. Valid for nitrate is that the electromotive force (e.m.f) between a nitrate selective electrode and a reference electrode is registered. An example of the structure of a nitrate selective electrode having good selectivity properties is disclosed in the British Patent GB 1.565.988. The amount of nitrate in the sample solutions can be calculated by measuring e.m.f in a number of solutions having known amounts of nitrate followed by a measurement of the e.m.f in the sample solutions. This procedure is not without objections. The membrane of the nitrate selective electrode is sensitive to disruptions in the form of deposits and functional disorders resulting from chemical depletion caused by continuous stirring or a continuously passing stream of sample and standard solutions. Other in the sample matrix occurring anions, such as chloride, also interfere with the measurement, which must be compensated for during the calibration of the electrode system. The Swedish Patent SE 9003014-9 discloses a way and a device to overcome some but not all of the above mentioned problems.

Valid for ammonium is that the electrochemical measurement is performed after a certain sample treatment. The ammonium ions are transformed into gaseous ammonia by increasing the pH to a value preferably exceeding 11.5. This is obtained by addition of sodium hydroxide. The ammonium electrode is at its measuring tool provided with a gas selective membrane through which the ammonia can diffuse inwards. Inside the electrode is a pH sensitive glass membrane with a weak buffer solution applied onto its surface. When the gaseous ammonia is absorbed by the buffer agent, the pH-value of the buffer agent changes as a result of reformation of ammonium ions. The change in pH is measured electrochemically according to the same principle as ordinary pH measurements using a glass electrode and a reference electrode (direct potentiometry). Reference is, for a complete disclosure of the working mode and the performance characteristics of the ammonium electrode, made to reviews and commercial data sheets, for example "Potentiometric Gas Sensing Electrodes", IUPAC, Selective Ion-Sensitive Electrodes, Cardiff, 1973, Butterworths, ISBN 0408705620, page 573 (authors J. W. Ross, J. H. Riseman and J. A. Krueger).

There is one further category of commercial nitrate indicators, namely those based on UV measurements. The nitrate ion exhibits typical absorbance characteristics in the ultraviolet area with an absorbance maximum at approx. 205 nm. The UV absorbance at one or more discrete wavelengths is measured and can thus be directly put in relation to the amount of nitrate in the sample. This measurement requires that the sample is free of substances and particles capable of absorbing or reflecting the high-energy UV radiation. Significant changes in the amounts of nitrate can easily be measured, even if the measurement, thus, not is free of objections from the aspect of selectivity in that safe determinations of amounts not can be done. The German Patent DE 324606 A1 discloses measuring principle and function of a representative measuring instrument based on UV detection.

O. Thomas et al give, in a scientific series of publications (Fresenius' J. Anal. Chem. 338:234-244, 1990), direction as how to overcome certain problems concerning varying background absorbance, as identified for the UV method above, by increasing the number of wavelengths within the UV area wherein absorbance measuring is performed. Disclosed are, furthermore, possibilities on how to mathematically calculate different UV absorbing compounds respective contribution to the total UV absorbance as measured. The authors give examples on how to make determinations of nitrate and chromate amounts. Even if all problems with background absorbing compounds are not solved, the result is improved by this method compared to measurements at only a few wavelengths. The possibility of determining chemical and biological oxygen demand (COD and BOD) is also discussed, but no convincing measurements are disclosed. A complete measuring spectrum in the area 205–250 nm, must during measurement of nitrate first be recorded for a standard solution (5 mg $NO_3^-$/liter). Pre-treatment of the sample is besides this not necessary, but a reduced conformity between the reference method and the disclosed method is obtained for samples with a high content of suspended substances. Certain sample matrices can, furthermore, demand modified standard solutions. Chromate determination, however, always requires addition of sodium hydroxide, to obtain a pH-value in the area of 9.0–9.5, prior to UV determination. The disclosed method only allows determination of one single parameter at a time and has no ability to per se indicate deviations in the sample composition caused by the presence of foreign UV absorbing compounds.

O. Thomas et al presuppose in their mathematical model that all disturbances caused by the presence of UV absorbing compounds and particles, influence recorded values for the UV absorbance equally in all samples—a presumption that strongly can be questioned. For each nitrate determination are 45 absorbance values in the wavelength area 205–250 nm recorded. A curve assumed to be possible to be described by means of a polynomial is obtained, if the recorded absorbance values are plotted as a function of the wavelength. A fourth degree polynomial is often enough to describe the background absorbance. Thomas method can not be used for detection of foreign compounds and is for untreated samples only applicable for nitrate determination.

B. J. Beemster and K. J. Schlager have disclosed an on-line method of determination of nitrate by UV measuring (American Water Association, Water Quality Technology Conference, Nov. 10–14, 1991, Orlando, Fla., U.S.A). The principle of the measuring method can be said to be an improvement of the method of O. Thomas as referred to above. Within the wavelength area of 200–800 nm are 1024 absorbance values recorded simultaneously during determination of a sample. A chemometric method of calculation is thereafter used. Certain wavelengths are in a first step selected. The absorbance values are thereafter pre-processed followed by a regression and a discriminant analysis. Predicated values are compared to manually compiled values and the prime combination of pre-process—analytical process is selected, i.e. the combination giving the least inaccuracy. A total of 30 calibration solutions, containing nitrate within a concentration of 0–500 ppm were used, of which 26 represent a so called learning set and the remaining 4 a test set. The predication error is said to be less than 1 ppm for nitrate within the concentration of 40–500 ppm. The authors, furthermore, draw the conclusion that the wavelength area of highest value for analytical utilisation is 220–250 nm. The objective of the further development work is said to be determination of further parameters for water samples using a minimum of calibration solutions.

The same authors state in a product data sheet for Chem-Scan™ UV-6100 Analyzer (Biotronics Technologies, Inc., Waukesha, Wis. 53186, U.S.A.) that also iron can be determined using the same technology as for nitrate. The number of determinations is said to be 256 and the wavelength interval to be 200–250 nm. Any exact calculation method besides "chemometrics" is not given in the product data sheet. Neither is the number of required determinations given.

The U.S. Pat. No. 5,242,602 discloses a further development of above disclosed method, but holds basically nothing new besides that the substances now determined are so called performance indicators, referring to various types of active chemical additives to aqueous solutions (column 4, line 55 of U.S. Pat. No. 5,242,602). These substances have typical absorbance properties in the UV and visible spectral area. Absorbance measurements are performed in the wavelength area of 200–2500 nm on homogeneous solutions free of particles. Calibration is done on solutions which were prepared using known amounts of these performance indicators and the searched amounts are calculated by means of chemometry. The invention is thus based on known technology and on a calculation method disclosed far earlier for a number of substances with a possible exception for performance indicators.

A problem not closely discussed in the U.S. Pat. No. 5,242,602 is the problem of particles or compounds capable of giving variations in background absorbance in the unknown sample. When matrix interferences are discussed, the effect thereof is described in terms of "background" and it is clearly disclosed that one condition for the quantification is that performance indicators absorb light in the wavelength area of 200–800 nm (column 5, line 8). The problem with performance indicators lost through precipitation is discussed to a certain amount but nothing is mentioned about inhomogeneous or particle containing samples.

The published International Patent Application WO 92/16828 discloses a measuring instrument for organic substances, preferably contaminations, in water samples, and a method of how to perform such measurements. The measurements are performed at discrete wavelengths within the UV area. Compensation is made for the sample's natural absorbance by a separate measurement in the visible area. The sample's turbidity is, furthermore, compensated for by a turbidity measuring in the infrared spectral area using a conventional detection at a 90 degree angle. The sample is preferably filtered before each measuring. The in the UV area recorded sample absorbance is revised with regard to visible natural absorbance and turbidity. The revised absorbance value is thereafter directly related to the sample's BOD (biological oxygen demand), COD (chemical oxygen demand) and TOD (total oxygen demand). How this is done is not at all disclosed, but it is reasonable to believe that a linear or near linear empirical relation exists. Chemometric calculation methods are not disclosed in this Patent Application.

Measuring of total phosphorous and total nitrogen requires sampling and extensive sample treatment making continuous in situ recording of these parameters impossible. The analyses are often performed at a laboratory and reporting of test results can be made on a time scale of hours after sampling. Reliable equipment for at-line or on-line measuring is here missing.

SUMMARY OF THE INVENTION

The objective of the present invention is to provide a method whereby many of above disclosed problems can be solved. It has now surprisingly been revealed that recorded test results as a whole, by means of one single direct measuring of the sample solution, can be mathematically processed resulting in that several quality parameters can be determined simultaneously.

Figure 1:
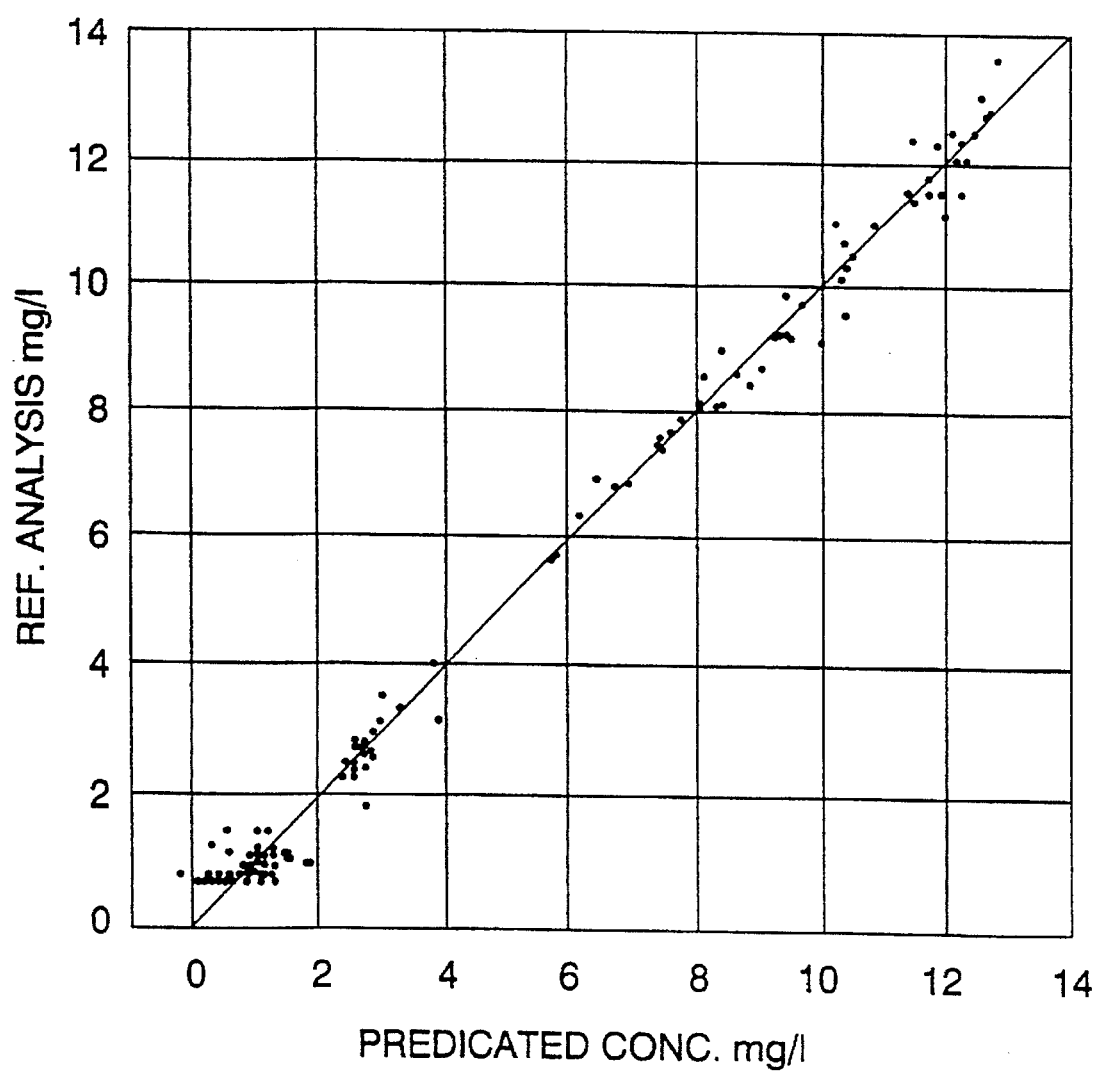
FIG. 1 is a graph illustrating the correlation between the amount of nitrate in a water sample measured by a reference analysis (REF. ANALYSIS) and the nitrate value measured by a PLS model (PREDICATED CONC.).

An essential part of the method according to the invention is to perform absorbance measurements at several wavelengths within the ultraviolet and/or visible spectrum simultaneously. Spectrophotometers suitable for this have for several years been commercially available and are well-known means for analytical chemists. Obtained test results have, however, mainly been used to determine the amount of one single substance by selecting one or several specific wavelengths. Remaining absorbance values have in certain cases been possible to use to revise for variations of unspecified background absorbance. This method can to a limited extent be used when minor variations in the sample matrix is anticipated. Thus, the U.S. Pat. No. 4,247,773 discloses how to determine the fat content of milk by absorbance measurements within the infrared spectrum at two selected wavelength areas, of which one area is used as reference. Since the absorbance is additive, successful trials have been made to determine the amount of several compounds in a sample. Each of the compounds thus contributes with its own specified absorbance at a certain wavelength and the amount of the respective compound can, when a series of absorbance values composed of respective absorbance value for the in the sample included compounds are recorded, be determined by solving the system of equations possible to compile. Multilinear regression (MLR) has been used for this purpose as disclosed above (DE 3324606 Al, O. Thomas et al., B. J. Bremster and K. J. Schlager). The method implies that the sample solution only contains exactly those compounds which are subject for determination and incorrect values for the amounts are obtained if unknown substances absorbing light at the used wavelengths are present in the sample solution.

Multilinear regression presupposes that determined quantities are non-correlated which they often not are. This can explain the limited success obtained in solving the problems of content determinations of water samples from for instance waste water purifying plants. The foundation for a more correct estimation of amounts in the sample solutions is laid by a mathematical-statistical manipulation of the total amount of recorded data followed by the possibility of describing the same by means of so called latent variables being orthogonal and entirely non-correlated. A model possible to use for this purpose is the so called Partial Least Square (PLS). A survey of the PLS model is given in for example "Multivariate Calibration" by H. Martens and T. Næs, J. Wiley & Sons Ltd, 1989.

An alternative mathematical-statistical model is Principal Component Regression (PCR). This model is described in the book "Chemometrics Tutorials" by D. L. Massart et al, Elsevier, 1990. Here the total amount of recorded data is also manipulated in that it can be described by means of so called latent variables being orthogonal and entirely non-correlated. A further possibility to make predications from recorded amounts of data is so called neural networks.

PLS, PCR and neural networks have successfully been used in combination with optical measurements within the infrared area (NIR—Near InfraRed). The U.S. Pat. No. 4,800,279 thus discloses how various physical quantities can be determined for instance for mixtures of hydrocarbons. The NIR method is less successful for aqueous solutions and for determination of the amounts of nutrient salts and no useful results are reported in said Patent. Water and carbon dioxide introduce problems being difficult to overcome; the U.S. Pat. No. 5,121,337 disclose a method of correction of spectral data. Successful use of PLS and PCR on water samples of the type disclosed in the present invention, has not yet been reported, probably due to problems with particles in the sample. NIR has been tried on such water samples, but gives a spectral information of such an insignificance that an evaluation is impossible to make. The U.S. Pat. No. 4,800,279 does, thus, not solve the analytical problem defined according to the present invention. The European Patent Application 0 404 562 also discloses the use of NIR and IR (mid InfraRed) to determine various parameters in samples, in this case certain specified biological samples. The invention of said European Patent Application is of the aforementioned reasons inoperative on samples which the present invention is intended for. It is the combination, unfiltered samples/several spectral measurements in the UV/visible area—PLS/PCR/neural networks-calibration with samples having known variable values, that gives the best characterisation of the present invention and which is not disclosed in any of the quoted references.

The invention will now be accounted for in detail and embodiment examples and test results will be disclosed. The method according to the invention is detailed for discrete and manually collected water samples, but the method is not limited to samples collected in this way and a continuous in situ measurement can also be at issue. The optical measurement can with regard to measurements of the latter type suitably be performed by means of fibre optics. Light source and light detector are located at a distance from the object to be measured, i.e. from the place where the water sample is located, while the measuring cell is placed in the water sample. Administration of sample into the measuring device can thereby be made completely automatically. The measuring device receives the light from the light source by way of one or more optical fibres. Light not absorbed by the sample is by means of the same principle returned to the light detector.

Absorbance data are during the calibration recorded for samples having known amounts of or measured values for nitrate, ammonium, orthophosphate, total nitrogen, total phosphorous, iron, COD, turbidity etc. within the wavelength area of 190–820 nm in steps of 2 nm. Air or distilled water can be used as reference. The number of samples used like this for calibration should preferably exceed 100 and the samples must, furthermore, be typical for the condition to be studied. The samples are preferably selected in such a way that too many samples having an almost identical composition are avoided. Standard methods as applied by authorised laboratories have been used to obtain said known amounts in and measured values for the samples.

Absorbance data are during measuring collected for unfiltered samples (air or water as reference) from several waste water purifying plants, whereby processing according to any of the models PLS, PCR or neural networks is made.

FIG. 1 shows the correlation between the amount of nitrate in a water sample from one purification plant measured by means of standard procedures (REF. ANALYSIS) and the nitrate values predicated by means of the PLS model (PREDICATED CONC.). Absorbance measurements have been made on unfiltered samples. The samples originate from three sampling sites in the waste water purifying plant: from incoming water having low amounts of nitrate and a high content of suspended particles, from an intermediate tank and from outgoing water having a higher amount of nitrate than incoming water but wherein the amount of suspended particles has been substantially reduced. Some samples are so called twenty-four-hour samples being analysed immediately, while so called one-week samples were preserved with sulphuric acid to inhibit the bacterial activity. Samples of both these type have been used during the calibration and the number of samples of each type were approximately the same. Very good correlation is, as can be seen, obtained.

Figure 2:
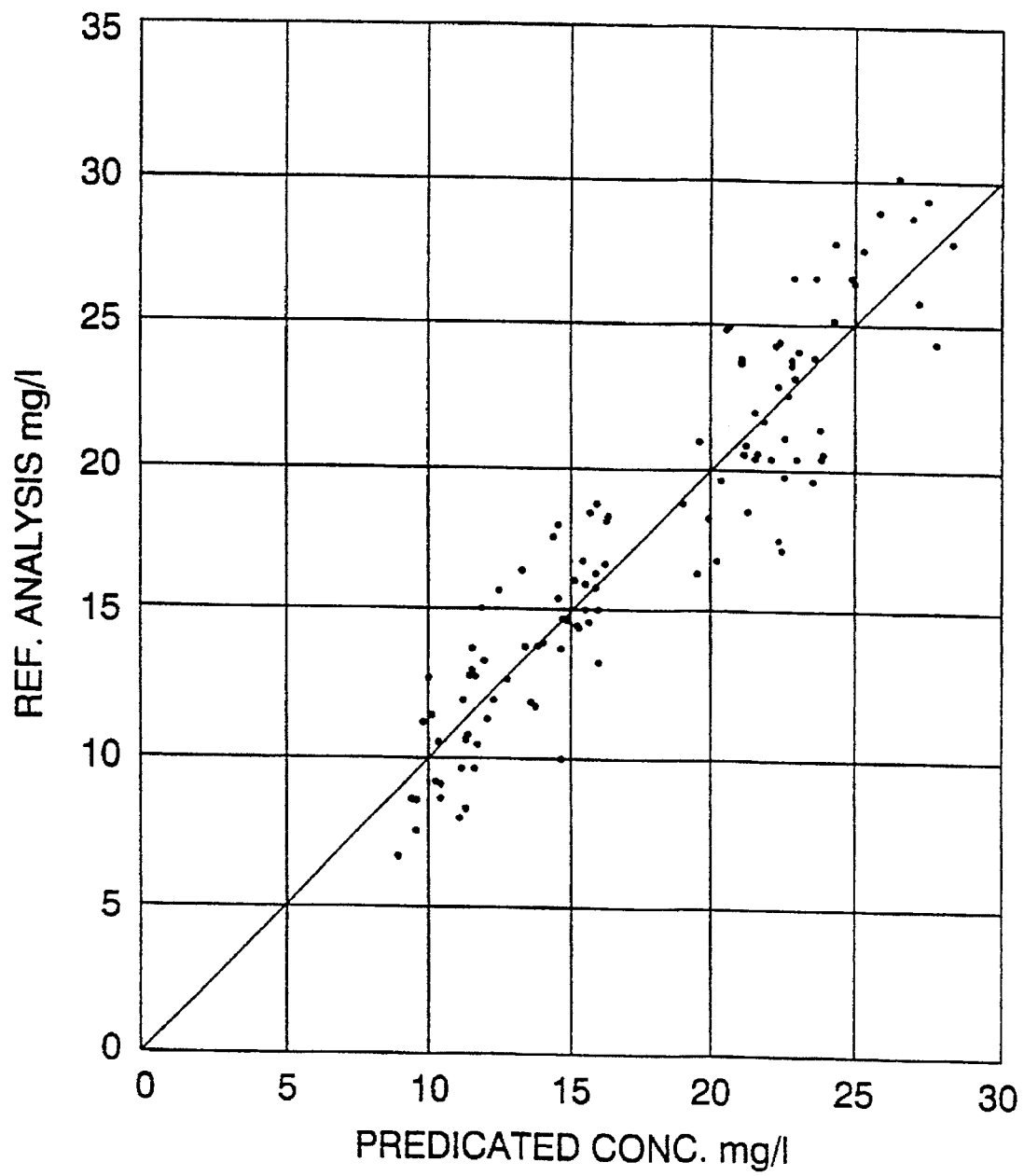
FIG. 2 is a graph illustrating the correlation between the amount of ammonium in a water sample measured by a reference analysis (REF. ANALYSIS) and the ammonium value measured by a PLS model (PREDICATED CONC.)
Figure 3:
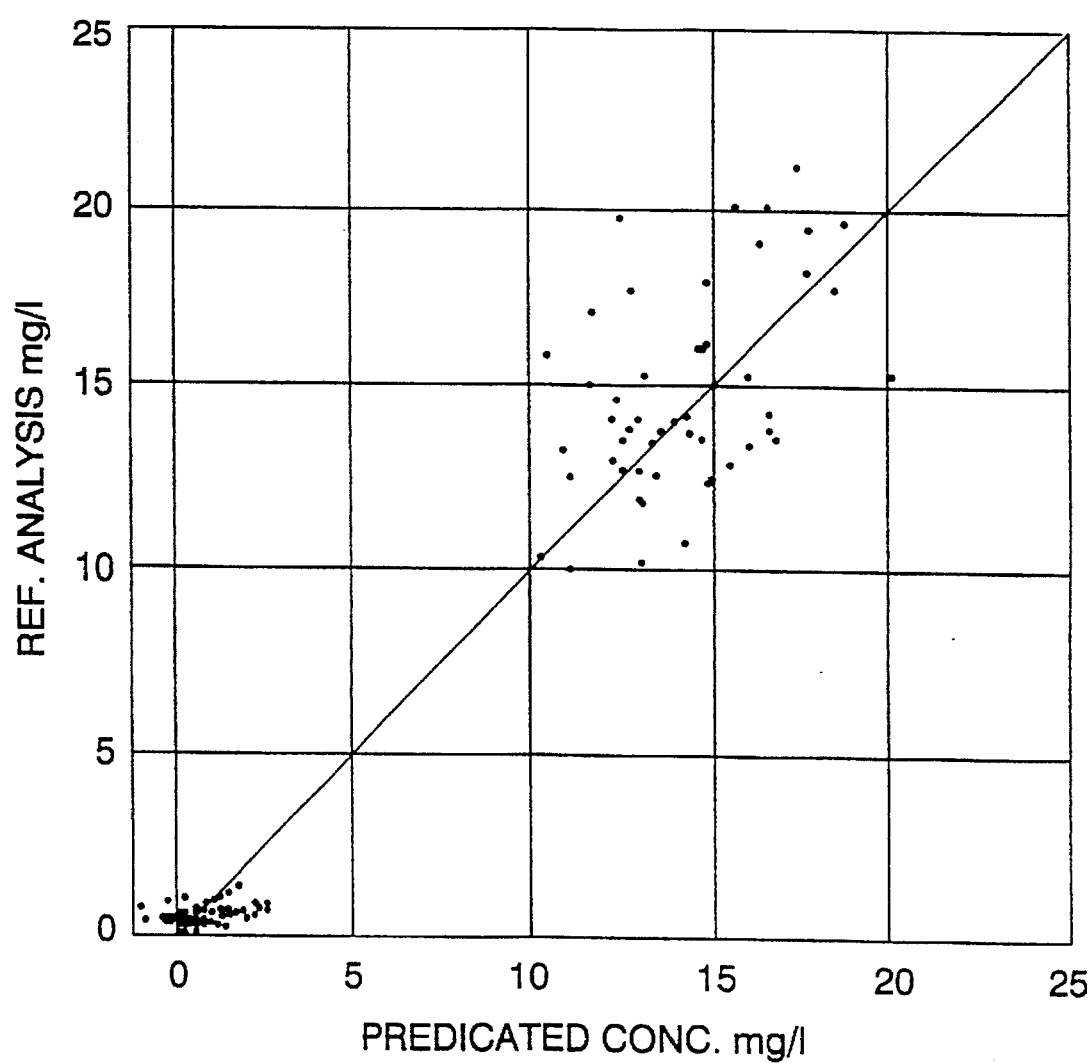
FIG. 3 is a graph illustrating the correlation between the amount of iron in a water sample measured by a reference analysis (REF. ANALYSIS) and the iron value measured by a PLS model (PREDICATED CONC.)
Figure 4:
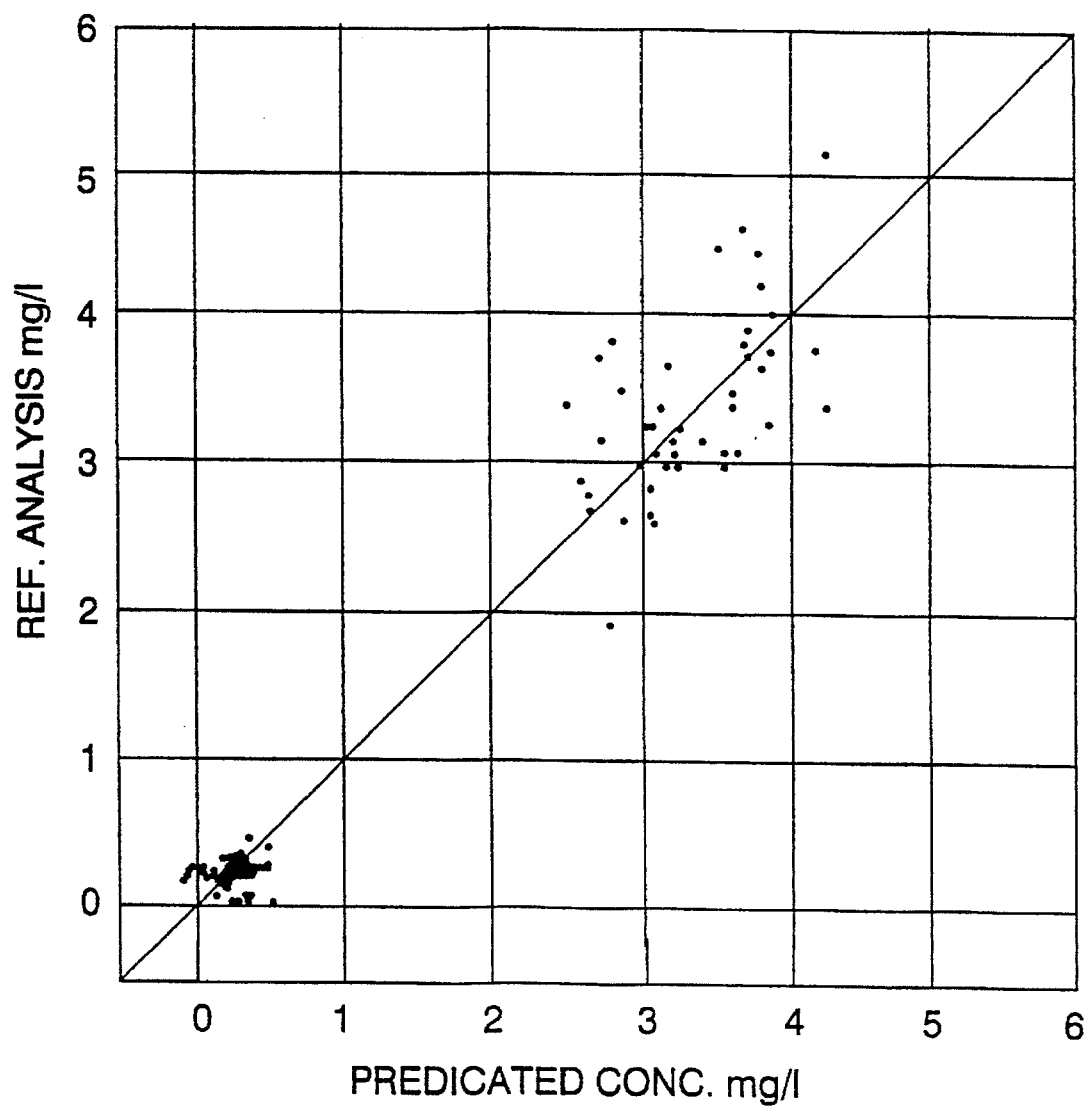
FIG. 4 is a graph illustrating the correlation between the amount of phosphorus in a water sample measured by a reference analysis (REF. ANALYSIS) and the phosphorus value measured by a PLS model (PREDICATED CONC.).

FIG. 2 shows corresponding correlation for ammonium, FIG. 3 for iron and FIG. 4 for total phosphorus.

Figure 5:
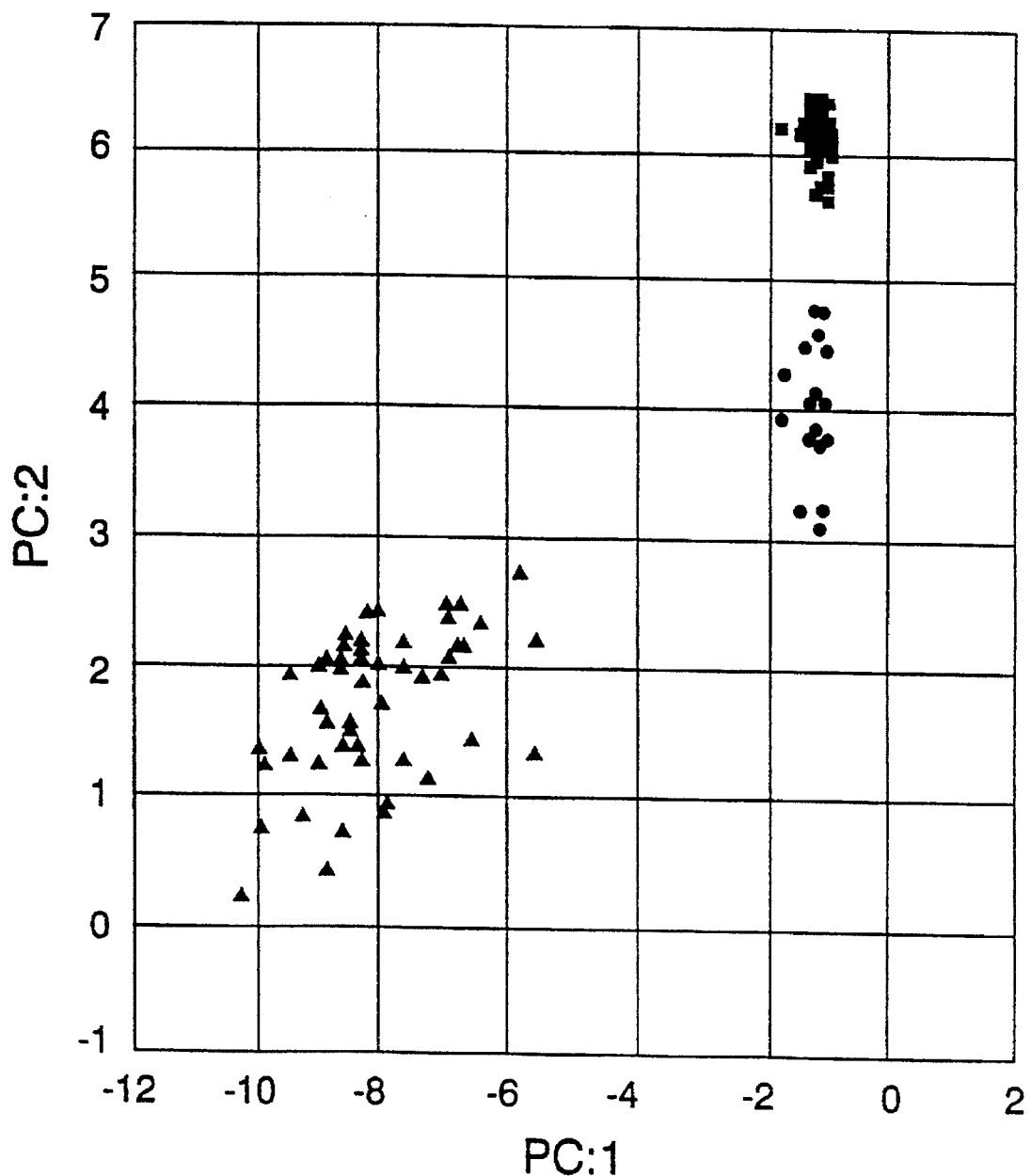
FIG. 5 is a calibration curve of the principal component i (PC:1) on the x-axis vs. the principal component 2 (PC:2) on the y-axis.

Water samples collected for chemical analysis and for analysis and treatment according to the present invention is classified based on the sampling site in the waste water purifying plant. Three classes of samples have thereby been studied: incoming water, intermediate tank water and outgoing water. The classification of unknown samples has been made after the calibration (see for instance H. Martens and T. Naes). The result from the calibration is given in FIG. 5. The Principal Component 1 (PC:1), which can be calculated from spectroscopic data and data from reference analyses by means of transformation into non-correlated latent variables, are plotted on the x-axis and Principal Component 2 (PC:2), also calculated, on the y-axis. The three classes are easy to distinguish: ▲ denotes samples representing incoming water, ● intermediate tank water and ■ outgoing water. Unknown samples can, after recording of absorbance values and data processing according to above disclosed method, be ranged into any of the three classes. The method can be based on other mathematical-statistical models as long as transformation into latent variables is performed in the model.

Figure 6:
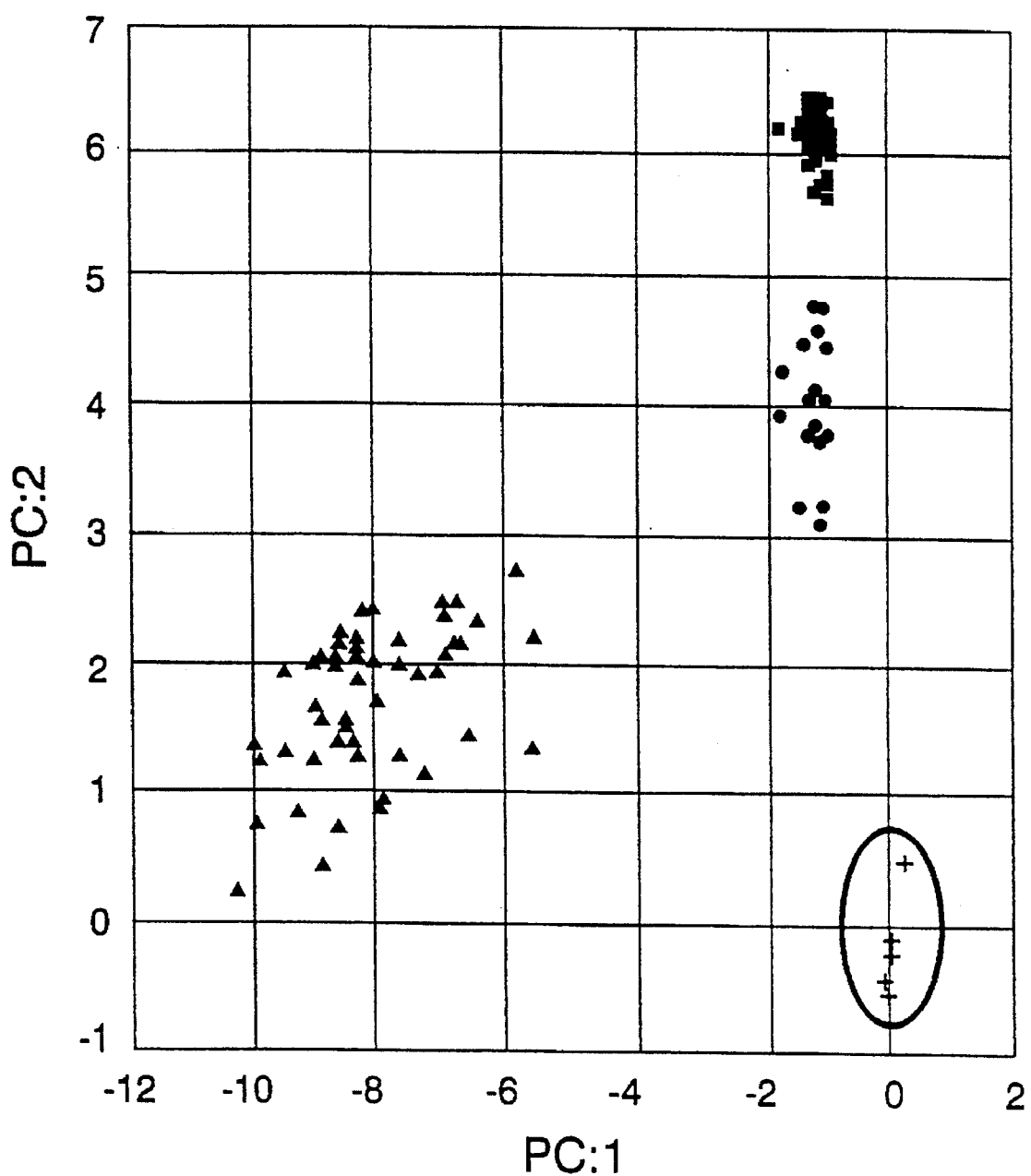
FIG. 6 is a calibration curve of the principal component 1 (PC:1) on the x-axis vs. the principal component 2 (PC:2) on the y-axis containing a minor amount of nitrobenzene.

FIG. 6 shows that some samples containing minor amounts of nitrobenzene can not be ranged into any of the three classes and for that reason can be identified as divergent (encircled points at the lower right corner of the Figure).

It is important to notice that above given examples are limited to for waste water purifying plants for relevant determinations of amounts and classifications, but that the evaluation includes water samples from several and various purifying plants. It is also important to establish that all determined amounts as well as the classification are made by using spectroscopic data from one single measuring. Furthermore, filtering of sample solutions having a high content of suspended substances and particles has not been made

We claim:

1. A method of determining physical and/or chemical properties in water samples containing suspended substances and/or particles, the physical and/or chemical properties being singly or jointly determined as amount of nitrate, iron, ammonium, phosphate, total nitrogen or total phosphorous; turbidity, chemical oxygen demand (COD) and/or biological oxygen demand (BOD), characterised in, (a) that all water samples are unfiltered and
   (b) that during an extensive calibration, involving a large number of water samples being typical for a condition to be studied and wherein physical and/or chemical properties have been determined by means of standard methods, is performed by spectroscopic absorbance measurements at several discrete wavelengths within ultraviolet and/or visible spectra, whereupon
   (c) sample evaluations continuously or intermittently are performed on water samples by means of spectroscopic absorbance measurements at several discrete wavelengths within ultraviolet and/or visible spectra and whereupon
   (d) all data obtained during the calibration and the sample evaluations together with numeric quantities giving the physical and/or chemical properties of the samples used during the calibration are processed by means of algorithms in a mathematical-statistical model.

2. A method according to claim 1 characterised in, that the calibration involves more than 100 water samples typical for the condition to be studied.

3. A method according to claim 1 characterised in, that the algorithms are algorithms in a Partial Least Squares (PLS) model.

4. A method according to claim 1 characterised in, that the algorithms are algorithms in a Principal Component Regression (PCR) model.

5. A method according to claim 1 characterised in, that the algorithms are algorithms in a neural network.

6. A method according to claim 1 haracterised in, that the spectroscopic absorbance measurements during the calibration are performed within a wavelength area of 190–820 nm.

7. A method according to claim 6 characterised in, that the spectroscopic absorbance measurements are performed in steps of 2 nm.

8. A method according to claim 1 characterised in, that a spectroscopic measuring cell is placed in the water sample, which cell by means of optical fibres communicates with a main measuring device.

* * * * *

UNITED STATES PATENT AND TRADEMARK OFFICE
CERTIFICATE OF CORRECTION

PATENT NO. : 5,641,966

DATED : June 24, 1997

INVENTOR(S) : Bo Karlberg, et al.

It is certified that error appears in the above-identified patent and that said Letters Patent is hereby corrected as shown below:

Column 1, line 8: "amounts/ of" should read --amounts of --

Column 2, line 51: "324606" should read --3324606--.

Column 8, line 44: "haracterised" should read --characterised--

Signed and Sealed this

Fourteenth Day of September, 1999

Attest:

Q. TODD DICKINSON

*Attesting Officer*    *Acting Commissioner of Patents and Trademarks*